United States Patent [19]

Cullimore et al.

[11] Patent Number: 5,187,072
[45] Date of Patent: Feb. 16, 1993

[54] METHOD AND APPARATUS FOR THE DETERMINATION OF FERMENTATIVE ANALYTIC CULTURED ACTIVITIES

[76] Inventors: D. Roy Cullimore, 2003 Styles Crescent E., Regina, Saskatchewan, Canada, S4V 0P8; George W. Alford, 1954 Old Daytona Rd., Daytona Beach, Fla. 32014; Abimbola T. Abiola, No. 12 Olonade Street, Ile-Ife, Nigeria; Jeff Reihl, 1005 Normandy Dr., Moose Jaw, Saskatchewan, Canada, S6H 3G8; Karim Naqvi, 7-2920 Victoria Avenue, Regina, Saskatchewan, Canada, S4T 1K7

[21] Appl. No.: 671,435

[22] Filed: Mar. 19, 1991

[51] Int. Cl.$^5$ ............... C12Q 1/04; C12M 1/24; C12M 1/34
[52] U.S. Cl. ................... 435/34; 435/291; 435/296; 435/287; 435/808
[58] Field of Search ................ 435/284–287, 435/291, 296–298, 34, 808

[56] References Cited

U.S. PATENT DOCUMENTS

| | | | |
|---|---|---|---|
| 2,476,093 | 7/1949 | Hirsch | 435/296 |
| 3,171,793 | 3/1965 | Searcy et al. | 435/34 |
| 3,474,003 | 10/1969 | Hirsch | 435/296 |
| 3,825,476 | 7/1974 | Hirsch | 435/296 |
| 4,868,110 | 9/1989 | Des Rosier et al. | 435/34 |
| 4,906,566 | 3/1990 | Cullimon et al. | 435/296 |

Primary Examiner—Robert J. Warden
Assistant Examiner—T. A. Trembley
Attorney, Agent, or Firm—James B. Middleton

[57] ABSTRACT

A method and apparatus for testing for the presence of selected microorganisms can be used in the field or in the laboratory. A sample to be tested is mixed with a culture medium for promoting growth of the selected microorganisms. A test device of a semi-permeable material is inverted in the culture medium, and the test device is held to a vertical position. The microorganisms create a biofilm within the test device, and the test device subsequently retains gas generated by the microorganisms. The gas lowers the density of the test device, causing the test device to float. The floating is taken as an indication of the presence of the selected microorganisms; and, by measuring the time required for the test device to float, the size of the population of the selected microorganisms can be determined.

11 Claims, 3 Drawing Sheets

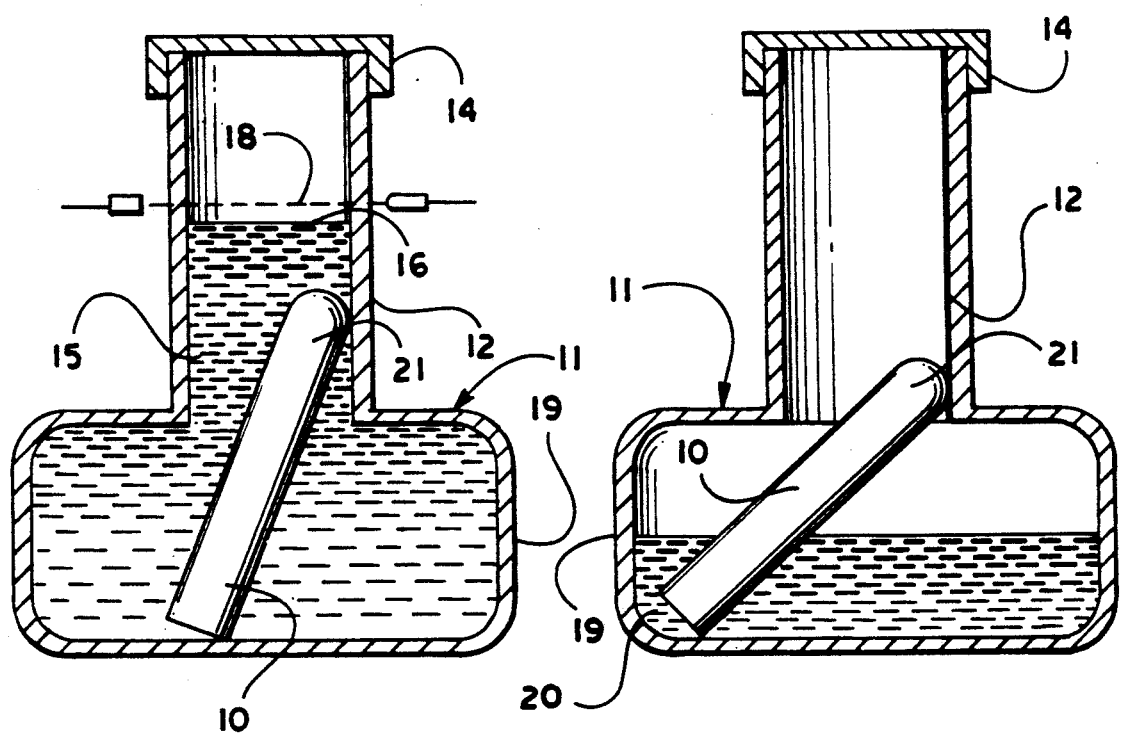
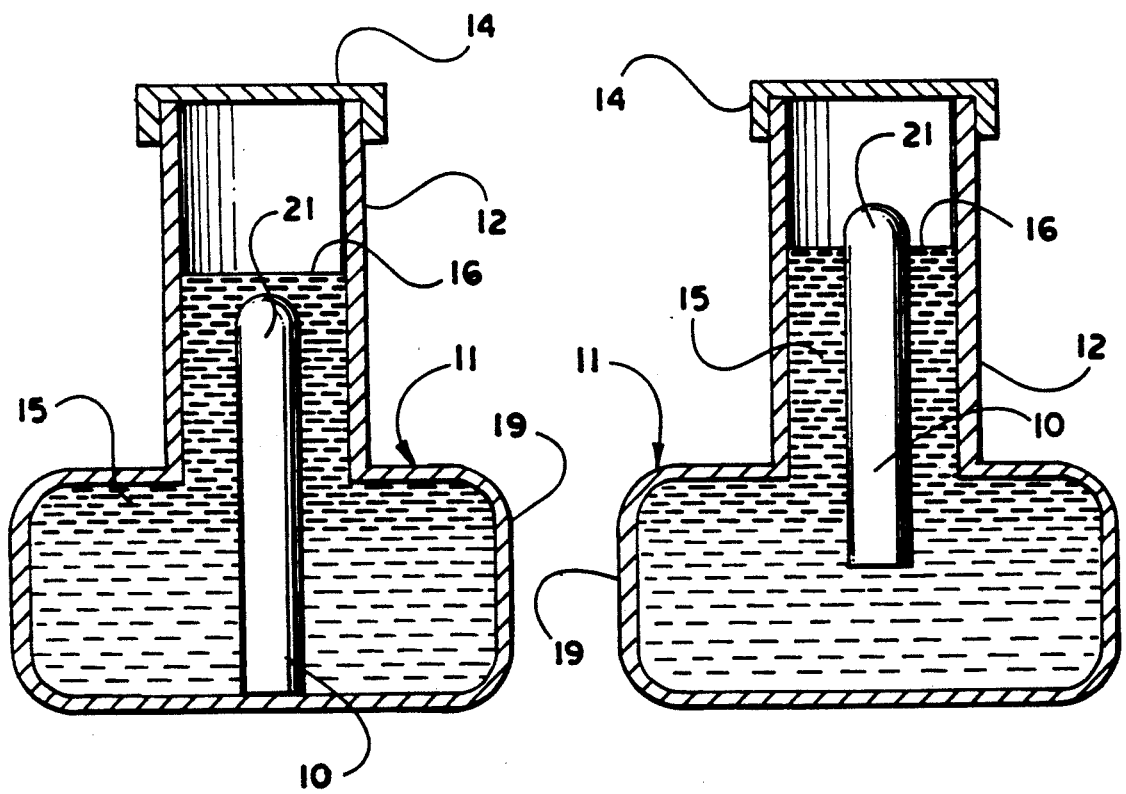

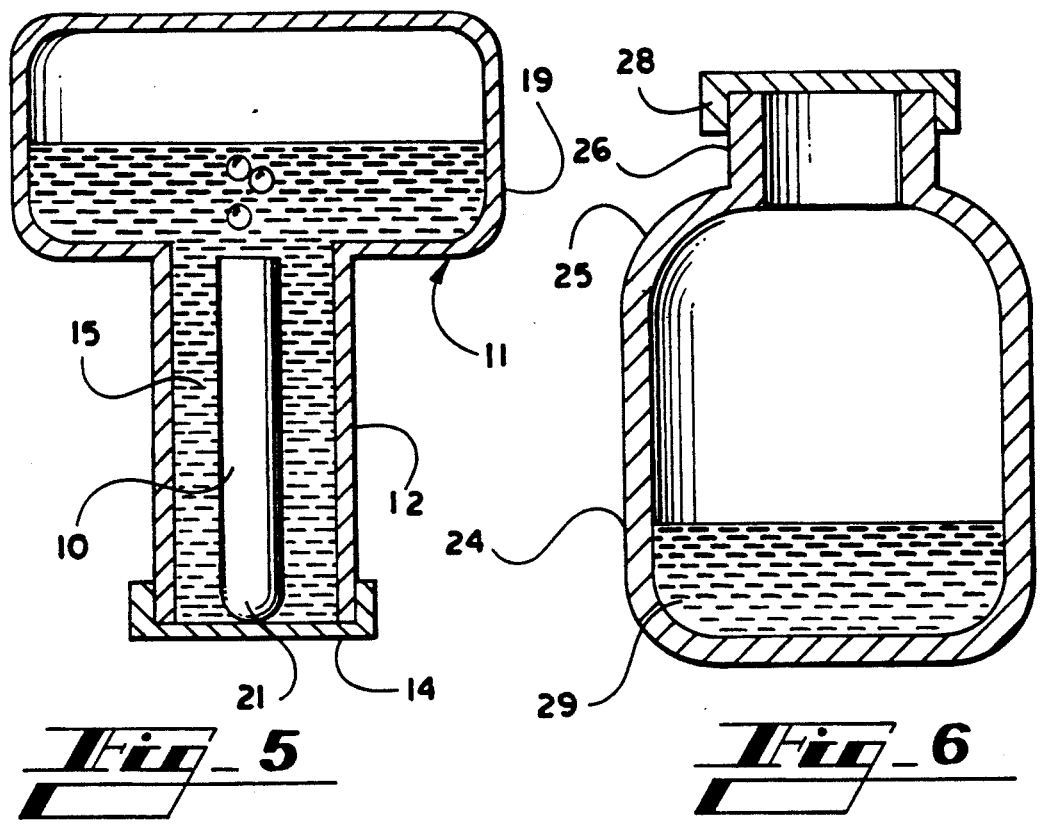
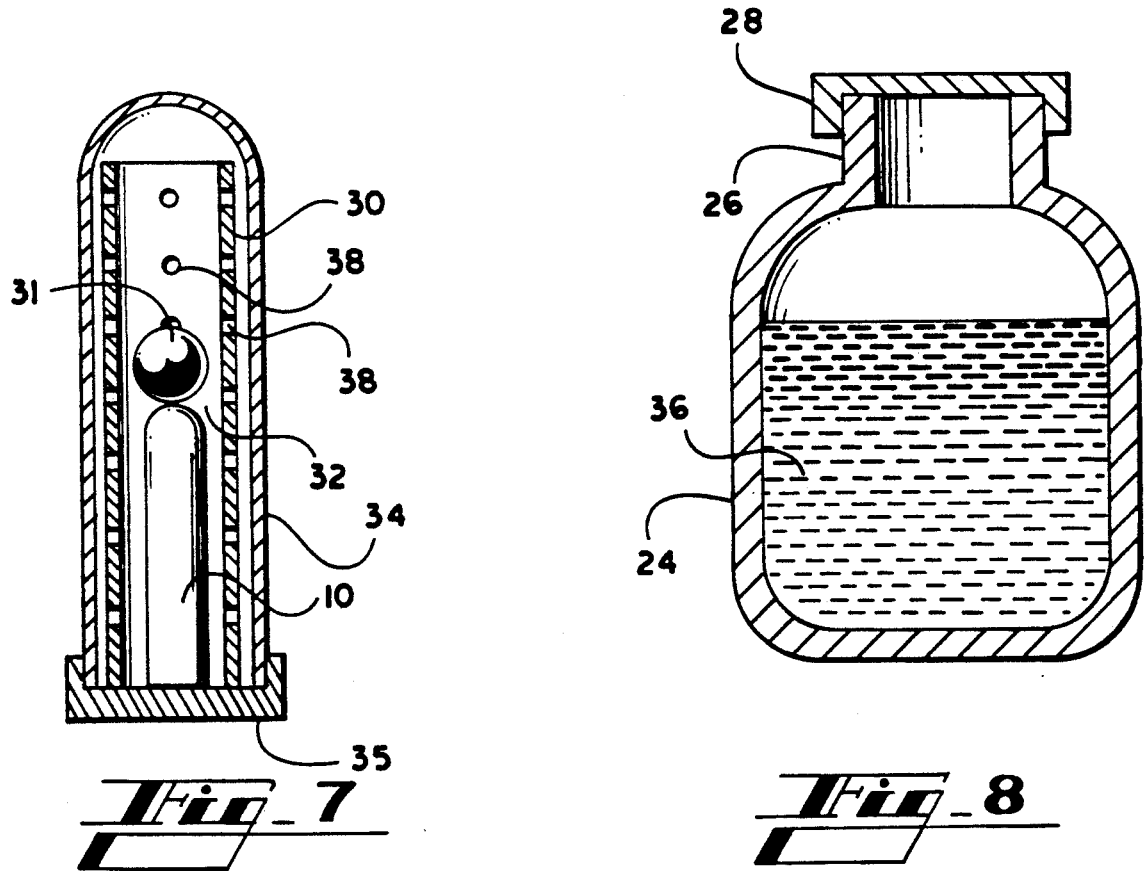

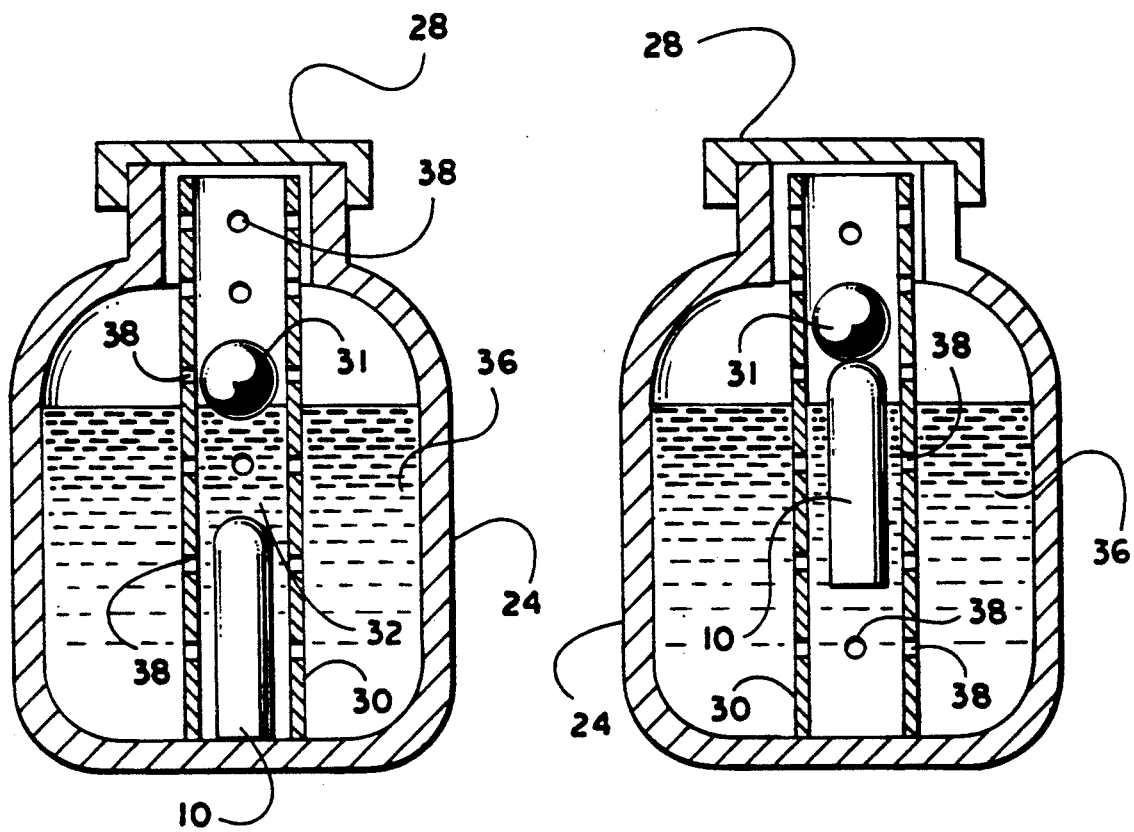

METHOD AND APPARATUS FOR THE DETERMINATION OF FERMENTATIVE ANALYTIC CULTURED ACTIVITIES

INFORMATION DISCLOSURE STATEMENT

Recent advances in microbiology have engendered many laboratory techniques useful to the engineer, microbiologist and various health specialists. A large number of tests is conducted daily, both in the field and in the laboratory. With the increasing awareness of potential sources of infection, there is an accelerating demand for screening of substances, notably of water to be used for drinking and the efficient disposal of hygienically hazardous liquids. However, due to the time required for the tests and the cost of many tests, complete testing is not economically feasible so that the tests may be run only on substances already under suspicion because of various observable evidence.

Those skilled in the art will realize that an incipient problem may not manifest itself in the natural state for one or more of various reasons, but the contamination may become obvious after some interference in the natural system. By way of example, bacteria may be present in small quantities, but not detectable through some understood biochemical function due to interferences from other organisms present, the inadequate ability of the cultural device to display in some form or other the affirmative occurrence, or cultural conditions unsuitable to yield the response.

The prior art includes culture systems for the entrapment of gases produced by bacterial activity in an inverted glass tube. Such a tube is ascribed to Durham, and is referred to as the Durham tube. This device does not encourage the movement of organisms into or out of the liquid constrained by the glass walls of the device. The generation of visible gas within a Durham tube may therefore be delayed or prevented by the lack of cellular and biochemical interplay between the bulk of the culture liquid and that constrained by the tube. The prior art does not address this concern, so the time of delay to the occurrence of gases (as individual or coalesced bubbles) cannot be quantified and used within a detection system. The prior art calls for quantification to be based upon either a statistical interpretation of a multiplicity of tests performed using different volumes of the given liquid, or upon the generation and enumeration of identifiable growths cultured directly or indirectly upon a culture medium appropriate for that purpose.

Information disclosing prior art can be found in the following articles:

APHA (1985) Standard Methods for the Examination of Water and Wastewater, 16th Edition, pp 1031-1032, APHA--AWWA, WPCF GELDRICH, E.E. (1990) Microbiological Quality Control in Distribution Systems. In Water Quality and Treatment. pp. 1113-1158 AWWA. McGraw Hill Publishers. SEIDLER, R.J. et al. (1981) Limitations of Standard Coliform Enumeration Techniques. *J. AWWA*. October 1981, pp. 538-542.

REASONER, D.J., J.C. BLANNON and E.E. GELDREICH (1979). Rapid Seven-hour Fecal Coliform. *Test Journal. Applied Environmental Microbiology*. Wm. C. Brown Publishing.

SUMMARY OF THE INVENTION

This invention relates generally to a method and apparatus for performing microbiological analysis, and is more particularly concerned with culture means for screening a sample effectively to determine the fermentative abilities through the generation of observable gaseous presences.

The present invention provides a method whereby a sample of material is placed within a test device, and one test can determine the presence or absence of the potentially gas generating group of organisms under facilitating cultural conditions. Furthermore, a quantification of the original population may be estimated statistically in cases in which the time of delay to the occurrence of determinable gas has been measured.

The present invention provides a test chamber having a partially or totally sunken test device within a liquid culture, the test device being, at least initially, semi-permeable to allow the covert passage of organisms into and out of the test device. Such passaging will allow the liquid medium constrained by the test device to be colonized to a similar extent to that of the containing culture liquid surrounding the device.

BRIEF DESCRIPTION OF THE DRAWINGS

These and other features and advantages of the present invention will become apparent from consideration of the following specification when taken in conjunction with the accompanying drawings in which:

FIG. 1 is a diametrical cross-sectional view of a culture chamber having a test device therein made in accordance with the present invention, and including the final volume of culture medium;

FIG. 2 is a view similar to FIG. 1, but showing the culture chamber before addition of the liquid sample;

FIG. 3 is a view similar to FIG. 1 showing the test device extending vertically due to initial generation of gas;

FIG. 4 is a view similar to FIG. 3 showing the test device floating due to the additional gas generation within the device;

FIG. 5 is a view similar to FIG. 1 showing the inversion of the chamber to remove any intrinsic air from the test device;

FIG. 6 is a different form of culture vessel, shown prior to being charged with the liquid sample and the test device;

FIG. 7 illustrates the test device presented in a format that will allow insertion into the culture vessel presented in FIG. 5 after the vessel has been charged with the liquid sample;

FIG. 8 is a view similar to FIG. 6 but showing the vessel after the addition of a liquid sample;

FIG. 9 shows the culture vessel of FIG. 8 after the insertion of the device in the format as shown in FIG. 7; and, FIG. 10 is a view similar to FIG. 9, but showing the test device after vertical movement due to gas production and entrapment.

DETAILED DESCRIPTION OF THE EMBODIMENTS

Referring now more particularly to the drawings, and to those embodiments of the invention here presented by way of illustration, it will be seen that the present invention includes a semi-permeable test device 10 within a test chamber 11. The physical arrangement is such that the test device 10 is prevented from taking up a lateral position by the narrow portion 12 of the chamber 11. The test device 10 is submerged in the liquid culture medium which rises up the narrow neck 12 of the test chamber 11. Aseptic conditions are maintained in that the test conditions are presented free from biological contamination and retained by the cap 14 of the vessel.

For an understanding of the invention, it should be recognized that, during culture, two microbiological events may occur. These are: firstly, the growth of organisms on the surfaces of the test device 10 through biofilm formation which will reduce the permeability of the test device 10 to chemical and biological entities; and, secondly, the device so biofouled becomes a repository for any gases generated by the incumbent biochemical activities. The product of these two events is that the test device 10, originally slightly more dense than the culture liquid 15, now has a reducing density as the gases form within the device 10. At some point in the diminution of density, the test device 10 will begin to float and will move to a vertical position. With further gas generation, the test device 10 will truly float, and will elevate to the surface of the liquid culture medium. The repositioning of the test device may be recorded visually after a standard period of time for a presence or absence determination. Alternatively, the precise time of the repositioning event may be recorded by such means as visual-image analysis or shifts in the conformity of a physical pathway such as a light beam. In the latter events the time of delay may be projected and the possible population of targeted organisms calculated statistically. The result is that fermentative gas producing biological events can be readily monitored in a given culture liquid and qualitative or quantitative interpretations appropriately made.

Thus, the present invention provides a test device 10 which will respond in a physical manner to the retention of any gases within the test device. At the same time gas is beginning to evolve, organisms may attach to the semi-permeable surfaces of the test device 10 and colonize, causing biofilms to establish along with a concomitant occlusion of the porous medium forming the semi-permeable barrier in the test device 10. As the density of the device 10 declines and, conversely, the buoyance increases with the increasing amounts of entrapped gas, so the device will change its position within the liquid culture medium 15 and elevate to break through the liquid-air interface 16. By selecting the appropriate cultural conditions for specific gas producing fermentative organisms, it becomes possible to detect these specific groups of bacteria both qualitatively and quantitatively. One mechanism for quantifying the population of the target group of bacteria is to time the delay period to a specific physical relocation event of the device 10. One such example is to measure the time of delay before the device 10 interrupts a light beam 18. As shown in FIG. 1 of the drawings, the light beam 18 is propagated by a light source 17 on one side of the test chamber 11, and received by a light detecting means 17' on the opposite side of the test chamber 11.

Looking specifically at FIG. 1 of the drawings, it will be noted that the test chamber 11 is in the shape of two interconnected cylinders. The lower cylinder 19 has a larger volume and a diameter exceeding, commonly by a factor of at least two, the diameter of the upper cylinder 12. It is structured in such a way that the device 10 cannot slide down to lie laterally on the floor of the lower cylinder 19. To achieve this, the length of test device 10 has to be greater than the sum of the diameter and the height of lower cylinder 19. It should be noted that the test device 10 has to remain sufficiently vertical to allow the entrapment of any gas generated within the test device 10.

As is illustrated in FIG. 2, prior to the charging of the vessel 11 with the liquid sample, the vessel will contain a concentrate 20 of the selective culture medium which will, upon dilution with the liquid sample, cause standard cultural conditions to be created in order to support the activity of the targeted organisms. At the same time, the test device 10 will not be totally immersed in the concentrated culture medium 20 but will extend into the atmosphere above the liquid. Some of this atmosphere may therefore become entrapped within the device and have to be expelled prior to the initiation of a test procedure.

It is contemplated that the test chamber of the present invention will be shipped and stored in the form shown in FIG. 2, and it will be understood that, conveniently, a selected culture medium can be placed in chamber 11 in either a concentrated liquid or a dehydrated form. The test chamber 11 created by cylinders 12 and 19 shown in FIG. 1 are also shown in FIG. 2, and it will be seen that water or other liquid is shown as added in FIG. 1 but is absent in FIG. 2. When liquid has been added, the test device 10 should sink to the bottom of the vessel.

Looking further at FIG. 1 of the drawings, it will be seen that the test device 10 consists of parallel walls and a hemispherical dome 21 at one end. Both the walls and the dome 21 are constructed of semi-permeable material to form a porous medium through which microorganisms can pass, and to which sessile organisms attach and form biofilms. It will of course be noted that the significant surface area presented by the device will allow a rapid colonization of the porous medium with occlusion occurring. The construction of the structural walls of the device therefore will allow initial passage of organisms through the walls of the device and into the interior of the device 10 which acts as a reaction chamber. Once occlusion has occurred, gases generated will be retained within the device 10.

Those skilled in the art will readily determine appropriate materials for the test device 10, but it is suggested that the device may be made of a hardened cotton cellulosic extraction, or a geotextile type Texel 440 PE 100-SSP, or a double rolled hardened low ash filter paper #52. It should be understood, however, that any material may be used so long as the material does not adversely affect the intended bacterial colonization, and does provide for the initial porosity, with subsequent occlusion and gas collection. A reasonably light weight is preferred to allow flotation of the test device after reasonable accumulation of gas.

Looking at FIG. 3 of the drawings, it will be understood that the device has now become coated with an expanding biofilm as cultural activities develop. It should be noted that the device 10 as illustrated occupies a vertical position with the domed end 21 uppermost, facing the air-liquid interface 16. As the cultured activities develop within the test device 10, any gas generated may rise to become entrapped under the dome 21. The initial effect will be to cause a loss in density so that the device now assumes a vertical position as shown in FIG. 3.

In FIG. 4 of the drawings, the test device 10 is again indicated as shown in FIG. 3 except that the amount of gas entrapped has become of a sufficient volume to cause the test device 10 to elevate to the liquid-air interface 16 to occupy a vertical position with the dome 21 extended into the atmosphere within the test chamber 11. During the movement of the device 10 upwards to the position shown in FIG. 4, it may be noted that the device will interfere with a light beam 18. Breaking of the beam 18 may be recorded by either the loss of intensity of the transmitted light passing through the upper cylinder to be recorded photometrically, or by a gain in reflected light recordable photometrically at an angle within the same horizontal plane as the original light beam. The time delay, from the charging of the test chamber 11 to the loss of the signal, may be used as either a quantitative or qualitative indicator of the presence of the targeted microorganisms.

FIG. 5 of the drawings illustrates the method by which any air initially trapped within the test device 10 can be released in order to allow the density of the device 10 to exceed that of the culture medium. When the charged device as shown in FIG. 1 is inverted, the trapped air will bubble out of the open end of the inverted test device 10, and the air bubbles will rise to the vessel's atmosphere. Once the trapped air has been vented, the vessel can be gradually restored to its upright position as shown in FIG. 1, and the incubation period for the test will be initiated.

In FIG. 6 of the drawings, an alternate culture vessel 30 is presented wherein both the liquid sample and the test device 10 are subsequently added to initiate the test procedure. A cylindrically shaped container 24 is displayed with inwardly sloping upper walls 25 terminating in a narrow neck 26 and cap 28. The concentrated liquid or desiccated culture medium 29 is present in the vessel.

FIG. 7 of the drawings illustrates a construction that allows the convenient carriage, packing and insertion of the test device 10 into the culture chamber 24. It can be seen from FIG. 6 that the device 10 could easily rotate and lie horizontally on the floor of the chamber 24. To prevent this, the insert device shown in FIG. 7 includes a cylindrical, perforated restrictor tube 30 constructed of a clear flexible material within which is the semi-permeable test device 10. Above the test device 10 is a low density floatable object 31 which will act as a visible magnifier of any elevation of the test device during the test. Perforations of at least 1 mm diameter and covering a minimum of 5% of the surface area of the restrictor tube are designed to allow movement of organisms into the zone 32.

A device as shown in FIG. 7 will, as is known by those knowledgeable in the art, be very prone to chance contamination unless the device is protected from such events. It is therefore proposed that the apparatus will be protected and retained in a sterile condition by storing the restrictor tube 30 with the test device 10 in a sterile tube 34. Aseptic techniques will be used concurrently with the removal of the cap 35.

Looking at FIG. 8 of the drawings, there is again the test chamber 24 in the modified form shown in FIG. 6, but with the liquid sample added to the culture medium to elevate the liquid level in the test chamber. Once the chamber has been so charged, the insert device shown in FIG. 7, including the restrictor tube 30, the test device 10 and the low density floating indicator device 31 will be placed into the chamber 24. To achieve this, the cap 28 is removed from the test chamber 24, and the cap 35 from the insert sterile tube 34. The sterile tube 34 is now aligned, open side down, over the open orifice of the charged test chamber 24. The tube and contents as shown in FIG. 7 are allowed to fall by gravity into the liquid culture medium 36 displayed in FIG. 8. Once the restrictor tube 30 and the contents have entered the liquid medium, the cap 28 is reapplied to the orifice of the test chamber 24.

Attention is directed to FIG. 9 of the drawings, which shows the test device 10 sitting in a vertical, sunken position within the restrictor tube 30, while the low density floating device 31 floats on the surface of the liquid culture medium 36. The perforations 38 allow the movement of organisms between the unrestricted culture medium in the chamber 24 and within the restricted liquid zone 32 confined by the restrictor tube 30. If the device 10 does not sink naturally, it may be considered that some air remains entrapped within the test device causing a premature and false buoyancy. To correct this, the same method can be applied as illustrated in FIG. 5 in which the vessel 24 is inverted in order to vent any entrapped air. It should be noted that one of the secondary purposes of the perforations 38 is to allow this vented air to diffuse easily, and to reduce the risk that the air will again become entrapped when the test chamber is restored to its upright position as shown in FIG. 9.

FIG. 10 of the drawings displays the typical type of reaction in which gas has been generated through the fermentative activities of the incumbent organisms. The test device 10 will gain in buoyancy as gas replaces liquid within the device 10. Once the device 10 elevates, it will break through the liquid-atmosphere interface within the restrictor tube 30 as a visibly distinguishable event. To magnify this occurrence, a low density device 31 floating within the zone of device elevation will be lifted higher, or out of the liquid to become clearly visible to the trained observer. This elevation of the floating device 31 can be used to generate a signal for the time of delay data, for example by interfering with an established physical system such as a beam of light.

Considering the test chambers as shown in FIG. 1 and FIG. 9, if a sample of water is to be tested, water will be placed into the test chamber 11 or 24, thereby dissolving or diluting the presented culture medium to achieve optimal concentrations for the differential biological culture to be undertaken. Such a dissolution or diffusive process will rapidly equilibrate the concentrations within the chamber, but such events will more slowly influence changes within the test device 10. The delay will be minimized by the utilization of semipermeable porous materials in the construction of the test devices and the admission of perforations to the walls of the restrictor tube 30. In both of the formats presented, the test device 10 may have a configuration resembling a thimble. When the test device is admitted, open side downwards, to the liquid culture medium, most of the entrapped air will pass outwards through the porous material of the device, leaving less than 25% of the internal volume of the device filled with air. This last air has to be removed by the method shown in FIG. 5. The test device 10 can be considered to have been successfully implanted only when the test device has sunk to the bottom of the charged test chamber. It will be evident to those conversant in the art that these thimble-like devices could be routinely maintained in a sterile and dried form for insertion into the charged liquid culture medium at the initiation of the test period.

In normal circumstances, the culture apparatus will be shipped with the culture medium in either a concentrated liquid, or a dried state. Where the former method is used, the thimble-like test device should be added to the liquid culture medium after the culture medium has been charged with such sterile water and liquid samples as may be necessary to achieve a culture medium at a dilution satisfactory to meet the cultural objectives necessary to maximize the selective nature of the test to encourage the generation of gases from the organisms targeted for determination.

A principal object of the present invention is to provide either a simple, low load field test method as a primary screening device or an automatic laboratory system in which the population size for the targeted biological group can be determined by the statistical interpretation of the time of delay to a positive reaction. Practice of this invention contemplates making the test results (automatic or manual) comparable to graphically presented standards along with tables and descriptors where required. Users will be encouraged to undertake comparable controls.

Since the microbial activity tests are designed around the apparatus of the present invention, there is a common sequence of the application to which variations are applied. The sample is applied to the selective culture medium and the incubation conditions are applied to maximize the potential for the target group of organisms to produce such volumes of gases (such as methane, hydrogen, nitrogen and carbon dioxide) within the thimble-like device that the density of the device falls to below that of the surrounding culture medium, so the device rises to the liquid-atmosphere interface and is maintained in the floating posture by the virtue of the retention of gases within the test device 10. The method as described is applicable in the determination of any microbial activity in which gases are evolved in such quantities as to exceed the saturation concentrations and appear as entrapped gas bubbles or vent to the atmosphere above the culture liquid.

As can be seen from the foregoing description, the present invention requires the characterization of some gaseous product of growth or activity within the apparatus to cause the observable physical shifting in the position of the gas entrapment device. By way of example, the following organisms may be determined by the appropriate application of the correct selective cultural and incubation conditions. Appropriate selection process may indicate the organisms listed:

| Media | Targeted Organism |
|---|---|
| Al Broth | Coliforms (37° C.) |
| Presence/Absence Broth | |
| Desoxycholate Broth | Fecal Coliforms |
| MacConkey Broth | (as for coliforms) |
| Brilliant Green Bile Broth | (45.5° C.) |
| Nitrate Broth | Denitrifiers |
| Organic medium with Formate, Citrate, Acetate at pH 6.5 | Methanogens |

Each of the above test systems achieves its uniqueness in function by the application of specific chemicals and culture media in an environment wherein the sunken thimble-like test device elevates to a floating position, which then indicates and confirms the presence and activity of the targeted group of organisms.

It will of course be understood by those skilled in the art that the particular embodiments of the invention here presented are by the way of illustration only, and are meant to be in no way restrictive; therefore, numerous changes and modifications may be made, and the full use of equivalents resorted to, without departing from the spirit or scope of the invention as outlined in the appended claims.

We claim:

1. A test apparatus for determining the presence of selected microorganisms in a given sample, said test apparatus comprising: a test chamber having a width, a liquid culture medium within said test chamber, said liquid culture medium being for promoting growth of selected microorganisms, a given sample being mixed with said liquid culture medium, and a test device within said test chamber, said test device having a length and consisting of an elongated semi-permeable tube having a closed end and an open end opposite from said closed end, said test device normally having a density slightly greater than the density of said liquid culture medium with said given sample mixed therewith, the arrangement being such that said selected microorganisms will generate gas within said test device thereby reducing the density of said test device to cause said test device to move up within said liquid culture medium with said given sample mixed therewith.

2. A test apparatus as claimed in claim 1, and further including means for preventing said test device from extending horizontally across said width of said test chamber.

3. A test apparatus as claimed in claim 2, wherein said means for preventing said test device from extending horizontally comprises a restrictor tube surrounding said test device, said restrictor tube being of a size to prevent said test device from extending laterally thereof, said restrictor tube being so dimensioned as to remain generally axially of said test chamber, said restrictor tube defining a plurality of holes therein for promoting contact of said liquid culture medium, with said given sample mixed therewith, with said test device.

4. A test apparatus as claimed in claim 3, said liquid culture medium having an upper surface within said test chamber, and said test apparatus further including a floatable device within said restrictor tube which floats on said upper surface of said liquid culture medium above said test device, so that when said test device moves up said test device will urge said floatable device upwards.

5. A test apparatus as claimed in claim 2 and including means for indicating the moving up of said test device, said means for indicating including a light source and light detecting means adjacent to said test chamber.

6. A method for testing to determine the presence of a selected microorganism in a given sample, said method comprising the steps of mixing a given sample with a culture medium for promoting growth of a selected microorganism, placing a semi-permeable test device within said culture medium and preventing said semi-permeable test device from lying horizontally within said culture medium so that said semi-permeable test device has a lower end and an upper end, said semi-permeable test device having a density greater than the density of said culture medium and having its upper end closed, and purging air from semi-permeable test device so that said test device sinks in said culture medium, allowing said selected microorganism to create a biofilm within said semi-permeable test device so that, subsequently, said semi-permeable test device will confine gas generated by said selected microorganism, and including the step of determining the presence of said selected microorganism by flotation of said semi-permeable test device caused by the gas generated by said selected microorganism.

7. A method as claimed in claim 6, wherein the said step of preventing said test semi-permeable device from lying horizontally consists of the step of holding said test semi-permeable device in a vertical disposition to prevent loss of gases generated within said test device.

8. A method as claimed in claim 7, and including the step of providing the test device with a perforate restrictor tube for carrying out the said step of holding said test device in a vertical disposition.

9. A method as claimed in claim 8 wherein said culture medium has an upper surface, and further including the step of floating a floatable device on said upper surface within said restrictor tube above said test device prior to the step of allowing said selected microorganism to create a biofilm, and detecting upward motion of said floatable device as an indication of the presence of said selected microorganism.

10. A method as claimed in claim 6 wherein said culture medium has an upper surface, and wherein said step of determining the presence of said selected microorganism consists of determining when said test device floats to said upper surface.

11. A method as claimed in claim 10, and further including the steps of measuring the time between said sinking of said test device in said culture medium and the floating of said test device to said upper surface, and determining the size of the population of said selected microorganism as a function of said time.

* * * * *